US006455713B1

(12) United States Patent
Monnier

(10) Patent No.: US 6,455,713 B1
(45) Date of Patent: Sep. 24, 2002

(54) REACTIVATION OF CS-PROMOTED, AG CATALYSTS FOR THE SELECTIVE EPOXIDATION OF BUTADIENE TO 3,4-EPOXY-1-BUTENE

(75) Inventor: John R. Monnier, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 09/152,124

(22) Filed: Sep. 14, 1998

(51) Int. Cl.$^7$ ............................ C07D 301/03; B01J 38/04
(52) U.S. Cl. ........................... 549/536; 502/34; 502/38; 502/53
(58) Field of Search ................... 502/34, 53, 344, 502/38; 549/532, 534, 536

(56) References Cited

U.S. PATENT DOCUMENTS

| | | | | |
|---|---|---|---|---|
| 3,899,411 A | * | 8/1975 | Bonacci et al. | |
| 4,011,180 A | * | 3/1977 | Lockwood et al. | |
| 4,033,903 A | * | 7/1977 | Maxwell | 252/476 |
| 4,049,539 A | * | 9/1977 | Yan et al. | |
| 4,094,889 A | | 6/1978 | Hayden et al. | 260/348 |
| 4,125,480 A | * | 11/1978 | Maxwell | 252/414 |
| 4,350,616 A | | 9/1982 | Boussert | 252/463 |
| 4,389,338 A | * | 6/1983 | Mitsuhata et al. | |
| 4,397,766 A | * | 8/1983 | Hawley et al. | |
| 4,555,501 A | | 11/1985 | Armstrong | 502/243 |
| 4,837,347 A | | 6/1989 | Rashkin | 549/534 |
| 4,906,600 A | | 3/1990 | Drake | 502/150 |
| 4,950,773 A | | 8/1990 | Monnier et al. | 549/534 |
| 5,081,096 A | | 1/1992 | Monnier et al. | 502/348 |
| 5,145,824 A | | 9/1992 | Buffum et al. | 502/216 |
| 5,155,242 A | | 10/1992 | Shankar et al. | 549/534 |
| 5,187,140 A | * | 2/1993 | Thorsteinson et al. | 502/348 |
| 5,362,890 A | | 11/1994 | Stavinoha, Jr. et al. | 549/536 |
| 5,391,527 A | * | 2/1995 | Kojima et al. | 502/53 |
| 5,525,740 A | | 6/1996 | Rizkalla | 549/534 |
| 5,618,954 A | | 4/1997 | Boeck et al. | 549/534 |
| 5,691,269 A | | 11/1997 | Rizkalla | 502/347 |
| 5,905,161 A | * | 5/1999 | Boeck et al. | 549/534 |

FOREIGN PATENT DOCUMENTS

| | | |
|---|---|---|
| DE | 43 39 168 | 5/1994 |
| EP | 0 141 596 | 5/1985 |
| WO | WO 89/07101 | 8/1989 |

* cited by examiner

Primary Examiner—Wayne A. Langel
Assistant Examiner—Christina Ildebrando
(74) Attorney, Agent, or Firm—Michael J. Blake; Bernard J. Graves, Jr.

(57) ABSTRACT

A method for restoring lost activity and selectivity of fresh cesium-promoted catalysts which comprises heating the catalyst at an elevated temperature in the presence of a sweep gas immediately prior to using the catalyst. The catalysts are particularly useful for the selective epoxidation of olefins to their corresponding olefin epoxides. Also described is a method for inhibiting or preventing deactivation of fresh Cs-promoted catalysts.

14 Claims, No Drawings

REACTIVATION OF CS-PROMOTED, AG CATALYSTS FOR THE SELECTIVE EPOXIDATION OF BUTADIENE TO 3,4-EPOXY-1-BUTENE

FIELD OF THE INVENTION

The present invention relates to a method for preventing or inhibiting deactivation of fresh Cs-promoted catalysts. The invention also relates to a method for restoring lost catalytic activity and selectivity of fresh cesium-promoted catalysts, particularly, fresh cesium-promoted, silver catalysts. The invention further relates to a method for preparing 3,4-epoxy-1-butene using the restored cesium-promoted, silver catalysts.

BACKGROUND OF THE INVENTION

Cesium (Cs) salt-promoted catalysts are typically used for the selective epoxidation of olefins to their corresponding olefin epoxides. For example, CsCl, CsOH, and/or $Cs_2O$ salts are used as silver (Ag) promoters for the selective epoxidation of ethylene to ethylene oxide; and CsCl is used as a Ag promoter for the selective epoxidation of butadiene to form 3,4-epoxy-1-butene.

Cs salts and Cs salt-containing compositions are known to be very hygroscopic and moisture-sensitive. Moisture-sensitivity can result in physical and chemical changes in Cs-containing compositions. Thus, Cs salt-promoted, Ag catalysts, for example, which are very active and selective for the epoxidation of olefins to their olefin epoxides, can lose their activity and selectivity when the promoter interaction of the Cs salt or Cs component with the Ag catalyst is lost or modified by the moisture-sensitivity of the Cs component.

SUMMARY OF THE INVENTION

It has been found that fresh Cs-promoted catalysts undergo loss of activity and selectivity for the selective epoxidation of olefins to their corresponding olefin epoxides upon storage under ambient conditions due to exposure to ambient moisture. It has been discovered that this loss in catalytic activity and selectivity can be prevented or inhibited by storing the fresh catalyst in a substantially moisture-free environment. It has also been surprisingly discovered that, if the catalyst has been exposed to moisture, and there is a loss of catalytic activity and selectivity, the initial catalytic activity and selectivity can be essentially completely restored by heating (calcining) the catalyst in the presence of a sweep gas at conditions effective to remove the moisture and restore the Cs-Ag promoter interaction.

Moisture-sensitivity and loss of activity/selectivity are related to the level of Cs salt promotion. Thus, catalysts promoted with higher levels of Cs salt deactivate upon storage more quickly than catalysts promoted with lower levels of Cs salt. However, all fresh Cs salt-promoted catalysts, regardless of the level of promoter loading, are moisture-sensitive and are prone to deactivation upon storage. Thus, all such catalysts would benefit from storage in a substantially moisture-free environment and/or from a calcination treatment to maintain and/or give optimum catalytic activity and selectivity.

Accordingly, in accordance with one aspect of the present invention, there is provided a method for preventing or inhibiting deactivation of fresh Cs-promoted catalysts. The method comprises the step of maintaining the fresh Cs-promoted catalyst in a substantially moisture-free environment until it is used.

In accordance with another aspect of the present invention, there is provided a method for restoring lost activity and selectivity of fresh Cs-promoted catalysts. The method comprises heating the catalyst in the presence of a sweep gas at conditions effective to restore the lost activity and selectivity immediately prior to using the catalyst.

In accordance with yet another aspect of the present invention, there is provided a method for preparing 3,4-epoxy-1-butene. The method comprises the steps of heating a fresh cesium-promoted, silver catalyst in the presence of a sweep gas at conditions effective to restore lost activity and selectivity of the catalyst; and, immediately thereafter, contacting 1,3-butadiene With oxygen in the presence of the catalyst at conditions effective to form 3,4-epoxy-1-butene.

As used herein, "fresh" catalyst means catalyst that has undergone all of the preparation steps including calcination to thermally reduce the valence state of the promoted metal and that is otherwise ready for use, except that it has not been contacted with reactive gases such as ethylene or butadiene under reaction conditions.

Also, as used herein, "immediately prior to" and "immediately thereafter" mean that the heat-treated catalyst has not been exposed to moisture for a period of time such that the restorative effect of the heat-treating step is lost.

Further, as used herein, "substantially moisture-free environment" means an environment that contains moisture at levels below that of ambient conditions.

DETAILED DESCRIPTION OF THE INVENTION

Without wishing to be bound by theory, it is believed that the moisture-sensitivity of the Cs salt promoter results in the migration and agglomeration of the promoter, either into "puddles" on the Ag surface, or from the Ag surface onto the support material such as $Al_2O_3$. Consequently, the promoter undergoes a transition from being optimally distributed in a two-dimensional array on the Ag surface to a situation where much of the Ag surface is not promoted. The result is lower activity and selectivity. Deactivation begins to occur for Cs-promoted, Ag catalysts as soon as they are prepared.

Various Cs-promoted, Ag catalysts as well as their methods of preparation are well known in the art. Representative Cs salt promoters include cesium nitrate, cesium chloride, cesium bromide, cesium oxide, cesium hydroxide, cesium acetate, cesium sulfate, cesium perrhenate ($Cs_2Re_2O_7$), and the like. Representative silver compounds include silver nitrate, silver oxalate, silver acetate, and the like. Such catalysts and their methods of preparation are described in the patent literature such as WO 89/07101 and U.S. Pat. Nos. 4,555,501; 4,950,773; 5,155,242; 5,362,890; and 5,691,269; the entire contents of which are hereby incorporated by reference.

The rate of deactivation of Cs-promoted, Ag catalysts is strongly ($>1^{st}$ order) and directly proportional to the level of Cs salt promotion. Thus, the moisture-sensitivity of the Cs salt promoter is an intrinsic property of all Cs salt promoted, Ag catalysts.

I have found that this moisture-induced deactivation can be prevented or inhibited by storing the fresh Cs-promoted catalyst in a substantially moisture-free environment until it is ready for use. As will be readily apparent to those skilled in the art, this moisture-free environment may be provided in various ways. For example, the fresh Cs-promoted catalyst may be stored in a vacuum desiccator or in a closed container containing desiccators. Preferably, the moisture-free environment has a moisture content of 1000 ppm $H_2O$ vapor or less.

If, however, the Cs-promoted catalyst has been exposed to moisture and has lost some of its initial activity/selectivity, I have surprisingly found that the Cs salt promoter can be very efficiently re-dispersed back on the Ag surface by simple calcination treatments in the presence of a sweep gas at elevated temperatures. The sweep gas may be any gas or gas mixture that is not reactive (i.e., inert) under calcination conditions, but is effective to remove moisture from the catalyst and restore the Cs-Ag promoter interaction. Such gas includes air, helium, hydrogen, oxygen, argon, carbon dioxide, nitrogen, and combinations thereof. Preferably, the sweep gas is air. Also preferably, the sweep gas has a moisture content of 1000 ppm or less.

The flow rate of sweep gas required in the process of the invention is a function of the amount of catalyst to be treated. This can be determined by routine experimentation by those skilled in the art. Generally, the sweep gas may have a gas hourly space velocity of about 10–10,000 $hr^{-1}$.

Preferably, the calcination is carried out at an elevated temperature between 150–350° C., and more preferably, between 200–300° C. It has been discovered that calcination in this temperature range can restore catalytic activity to levels between 85–100% of that for freshly prepared catalyst.

The length of time needed to restore catalyst performance is related to the temperature of calcination. For example, air calcination at 225° C. requires 4–8 hours to give approximately 95–100% restoration of activity, while calcination at 250° C. requires only 1–2 hours. Thus, lower calcination temperatures would require longer calcination periods, and vice versa.

The specific length of time required to restore the catalyst to its initial activity/selectivity also depends on the amount of catalyst deactivation. Generally, calcination for a period of 1–30 hours at the above temperatures would be sufficient. Preferably, the heat treatment is carried out for a period between 4–23 hours, and more preferably between 4–15 hours.

The restorative calcination step may be carried out in a batch, semi-continuous, or continuous mode of operation. For example, batch operation may comprise heating the catalyst at the requisite temperature in a tubular reactor vessel while introducing a stream of air into the reactor. After the activity and selectivity of the catalyst have been restored, the flowing air may be stopped and the reactive gases such as ethylene or butadiene and oxygen plus an optional diluent may be introduced into the reactor to initiate the desired reaction.

Thus, another aspect of my invention relates to the preparation of 3,4-epoxy-1-butene. This embodiment may be carried out by contacting 1,3-butadiene with oxygen in the presence of the heat-treated catalyst described above at conditions effective to produce the 3,4-epoxy-1-butene. The specifics for carrying out this reaction are well known in the art and are described in the patent literature such as U.S. Pat. Nos. 4,950,773; 5,117,012; and 5,618,954; the entire contents of which are hereby incorporated by reference.

As an optional step, the heat-treated catalyst may be intimately contacted with a gas stream comprising about 4 to 50% by volume of hydrogen at a temperature of about 170° C. to 400° C. and a gas hourly space velocity of about 10 to 10,000 $hr^{-1}$ to further improve or enhance the activity/selectivity of the catalyst. The balance of the gas stream can be any inert gas known in the art such as nitrogen, helium, argon, carbon dioxide, methane, or a mixture thereof. This $H_2$ treatment step may be carried out in accordance with the teachings of U.S. Pat. No. 5,081,096; the entire content of which is hereby incorporated by reference. I have found that Cs-promoted catalysts given this $H_2$ treatment after the heat treating step can activate more quickly, and possibly even to a higher level of catalytic activity, than heat-treated Cs-promoted catalysts not given the additional $H_2$ treatment.

While the foregoing discussion has been focused on Cs-promoted, Ag catalysts, it is believed that all fresh Cs salt-promoted catalysts are moisture-sensitive and are prone to deactivation upon storage at ambient conditions. Thus, all such catalysts would benefit from storage in a substantially moisture-free environment and/or a calcination treatment immediately prior to being used to give optimum catalytic activity and selectivity greater than otherwise observed.

My novel method for restoring the activity and selectivity of Cs-promoted catalysts is further illustrated by the following examples.

EXAMPLES

Catalyst Preparation

CsCl-promoted, Ag catalysts supported on SA-5562 alumina (from Norton) were used in the following examples. Unless otherwise indicated, the catalysts were prepared in the manner described below.

A silver oxalate solution was prepared by dissolving 149.0 grams of silver oxalate in a solution (maintained at 10° C.) of 118 grams of ethylenediamine plus 165 grams of water. The solution was stirred vigorously until the silver oxalate was completely dissolved. To this solution, 2 mls of an aqueous solution containing 0.960 grams of CsCl were added in a dropwise manner.

600 grams of SA-5562 alumina rings (from Norton) were added to the above solution. The relationship between total pore volume of the SA-5562 alumina rings (¼" diameter) and the total volume of silver oxalate+CsCl solution resulted in essentially total uptake of the liquid solution into the pores of the SA-5562 support. To ensure complete penetration of the solution into the support pores, the impregnated catalysts were subjected to three vacuum-vent cycles to evacuate-force the solution into the pores. The small excess liquid solution was decanted and the wet impregnated rings were dried in a forced-air Blue M, Model 460A-3 convection oven at 60° C. The impregnated catalysts were placed in 4 mesh, stainless steel, baffled drums and tumbled slowly from 30 minutes to accelerate drying.

The free-flowing dried catalyst rings were placed in a 3" O.D.×10" long Pyrex tubular container that was positioned in a split-tube furnace. Thermocouples were placed at the 1", 5", and 8" position in the catalyst precursor bed. The catalyst rings were heated in flowing air [800–1000 cc/min (STP)] to a final temperature of 280–310° C. using a temperature ramp rate of 2–3° C./min. The temperature was maintained at 280–310° C. for 2 hours before being cooled to 25° C. The catalyst was then ready for use and was stored in amber glass bottles.

An analysis of this catalyst showed that it contains 14.2% (wt) Ag and 1046 ppm (wt) Cs. Target values were 15.0% (wt) and 1000 ppmw, respectively.

Evaluation Method

For catalyst evaluation, catalyst samples were ground and sieved to 10/20 mesh (2.0–3.2 mm in diameter) and loaded into a Pyrex tubular reactor. The dimensions of the tubular reactor were 30.5 cm in length with an inside diameter of 1.0 cm. Typical catalyst sample sizes were 3.0 grams. The catalyst was maintained at the correct position in the tubular reactor by a coarse Pyrex frit which was fused in the Pyrex tubular reactor. A Chromel/Alumel alloy thermocouple sheathed in stainless steel was embedded within the middle of the catalyst bed to measure reaction temperature. The empty reactor volume above and below the catalyst bed was filled with Pyrex glass beads to ensure that thermal reactions in such empty volumes did not occur.

The results reported in the following examples were obtained while operating at steady state conditions using a pressure of 1 bar absolute (1 atmosphere) in a single-pass, flow reactor. The mixture of inert diluent, butadiene, and oxygen was fed to the reactor using mass flow controllers in a diluent:butadiene:oxygen molar ratio of 4:1:1 at an overall flow rate of 300 ml (at standard temperature and pressure) per minute. The mass flow controllers provided highly accurate and reproducible flow rates regardless of pressure changes from the supply cylinders or the reactor system downstream from the flow controllers. The 300 ml (STP) per minute rate of feed gas mixture gave a gas hourly space velocity (GHSV, volume of gas fed per hour per volume of catalyst) of 4500 $hr^{-1}$. Organic halide (2-chlorobutane) was added to the reactor feed gas in a stream of helium containing 100 ppmv 2-chlorobutane. Thus, a mass flow controller was set to provide a flow rate that gave organic chloride concentrations of 1 to 20 ppmv in the feed gas.

Analyses of the reaction products and feed compositions were performed using an in-line gas sampling loop connected directly to the inlet of a Hewlett-Packard 5890 gas chromatograph. Thermal conductivity (TC) was used to analyze all of the reaction products. The TC detector gave quantitative analyses for oxygen, carbon dioxide, water, and epoxybutene. Further, by means of a switching valve, it was possible to divert the feed stream through the in-line sample loop prior to passage over the catalyst. In this way, quantitative analysis of the feed stream and comparison to the corresponding data from the reactor effluent were-possible, thereby providing very accurate measurements of both conversion levels and product selectivities. Output from the TC detector was integrated using an HP 3396 computer/integrator which was programmed to give both absolute quantities and rates of formation. All reactor exit lines were heated and maintained at 125–140° C. to prevent product condensation.

The GC analysis was performed using the following temperature programming schedule: an initial temperature of 100° C. was held for 2 minutes, followed by a temperature program rate of 10° C./min up to a final temperature of 200° C. which was then held for 7 minutes.

As used herein, conversion is the mole percent conversion of butadiene defined as:

$$\frac{\text{Moles butadiene converted to products}}{\text{Moles butadiene fed}} \times 100$$

and selectivity is the percent selectivity to 3,4-epoxy-1-butene defined as:

$$\frac{\text{Moles butadiene converted to 3, 4-epoxy-1-butene}}{\text{Moles butadiene converted to total products}} \times 100.$$

Example 1

Catalyst prepared as described above (14.2 wt % Ag, 1046 ppmw Cs) was ground and sieved to 10/20 mesh. 3.0 grams were loaded into a Pyrex reactor. The sample was heated to 200–205° C. in a gas stream of 80 cc/min (STP) helium and 20 cc/min (STP) hydrogen. The catalyst was maintained at 203° C. for 1 hour. After 1 hour, the $H_2$ was removed from the flow stream and the catalyst cooled to 190° C. by adding 120 cc/min helium, 50 cc/min butadiene, and 50 cc/min oxygen (all flows at STP conditions), plus 2 ppmv 2-chlorobutane to the 80 cc/min of helium already present, to give a total flow rate of 300 cc/min (STP). Reaction temperature was increased to 225° C. and the catalyst was allowed to reach steady-state conditions before performance data were recorded. The results of the above catalyst after four different evaluations are summarized in Table 1. The reaction conditions for all four evaluations were a temperature of 225° C. and a total flow of 300 cc/min (STP).

TABLE 1

| Age of Catalyst (days) | % Butadiene Conversion | % Epoxybutene Selectivity |
|---|---|---|
| 1 | 12.0 | 94.7 |
| 17 | 5.2 | 92.1 |
| 21 | 3.2 | 90.7 |
| 86 | 2.4 | 90.6 |

The results in Table 1 show a dramatic loss in catalytic activity and selectivity of a catalyst stored for 86 days in an amber glass bottle at ambient laboratory conditions of moisture and temperature.

Example 2

Two hundred (200) grams of the catalyst of Example 1 after 17 days of storage were placed in the calcination tube described above and were heated to 240° C. in 1000 cc/min (STP) flowing air for 2 hours before being cooled to 25° C. in the flowing air. This catalyst was immediately re-evaluated at 225° C. to give a steady-state activity of 11.0% butadiene conversion and 94.4% selectivity to epoxybutene.

These results indicate that the post-treatment in flowing air at 240° C. for two hours increased catalytic activity from 5.2% conversion to 11.1 % conversion, while the selectivity also increased from 92.1% to 94.4%. In addition, the activity following the post-treatment in air was only slightly less than the activity of the catalyst immediately after preparation, i.e., 11.1% conversion versus 12.0% butadiene conversion.

Examples 3–4

The catalyst sample of Example 2 was divided into two portions. One portion was stored in an amber bottle with the lid placed loosely on top of the bottle. The second portion was also placed in an amber bottle, and the bottle with the lid placed loosely on top was stored in a vacuum desiccator filled with desiccant and maintained at 30 inches of vacuum. Each sample was periodically evaluated at the conditions described above, and the results are summarized in Table 2. The evaluations were made with 3.00-gram samples at 225° C. The results reported were at steady-state conditions.

TABLE 2

| No. of Days of Storage After Post-Treatment at 240° C. | Stored in Vacuum Desiccator | | Stored in Lab. Air at Ambient Conditions | |
|---|---|---|---|---|
| | % Butadiene Conversion | % Selectivity to Epoxybutene | % Butadiene Conversion | % Selectivity to Expoxybutene |
| 0 | 11.1 | 94.4 | 11.1 | 94.4 |
| 3 | — | — | 97 | 92.8 |
| 4 | 9.8 | 93.3 | — | — |
| 7 | 10.0 | 92.9 | 9.4 | 92.6 |
| 15 | 10.7 | 93.6 | 6.7 | 92.6 |
| 21 | 10.8 | 93.1 | — | — |
| 24 | — | — | 6.5 | 92.5 |
| 29 | 11.2 | 93.9 | — | — |
| 43 | 10.2 | 92.9 | 4.9 | 92.4 |
| 100 | 7.3 | 92.0 | — | — |
| 105* | 12.7 | 94.3 | — | — |

*Catalyst was given an "in situ" treatment in flowing air at 250° C. for 1.0 hour immediately before evaluation.

The results in Table 2 indicate that storage in a moisture-free environment results in catalysts having superior storage properties as manifested by maintenance of catalytic activity and selectivity for at least 43 days of storage. Further, these results indicate that activity of the deactivated samples can be reactivated at least a second time by a similar post-treatment in air.

Examples 5–11

Effect of Calcination Temperature

Portions of the catalyst that had been stored in amber bottles at ambient conditions described above were evaluated in the same manner as in Example 1 with the calcination post-treatments summarized in Table 3 below. The calcination gas composition used in the post-treatments consisted of 50 ml/min (STP) $O_2$ and 200 ml/min (STP) helium.

TABLE 3

| | Calcination Conditions | | Butediene Conversion | Epoxybutene Selectivity |
|---|---|---|---|---|
| Example No. | Temp. (° C.) | Time (hrs) | (%) | (%) |
| 5 | none | none | 2.7 | 91.1 |
| 6 | 175 | 1.0 | 5.2 | 92.4 |
| 7 | 225 | 1.0 | 8.6 | 92.4 |
| 8 | 240 | 1.0 | 9.3 | 93.3 |
| 9 | 275 | 1.0 | 8.5 | 93.7 |
| 10 | 300 | 1.0 | 9.6 | 93.4 |
| 11 | 350 | 1.0 | 6.5 | 93.2 |

The results in Table 3 illustrate that post-treatments as low as 175° C. prior to reaction increase both catalytic activity and selectivity to epoxybutene. Temperatures as high as 350° C. are also beneficial in improving activity (conversion of butadiene) and selectivity to epoxybutene, although temperatures in the range of 225° C.–300° C. are most optimal.

Examples 12–17

Effect of Calcination Time

Portions of the catalyst described in Example 1 were evaluated after calcination post-treatments at 225° C. for different lengths of time. In these examples, the calcination gas composition was 20 ml/min (STP) $O_2$ plus 80 ml/min (STP) helium. The results are shown in Table 4 below.

TABLE 4

| Example No. | Length of Calcination (hrs) | Butadiene Conversion (%) | Epoxybutene Selectivity (%) |
|---|---|---|---|
| 12 | 0 | 3.1 | 91.5 |
| 13 | 1 | 9.0 | 94.5 |
| 14 | 4 | 12.8 | 94.3 |
| 15 | 8 | 13.5 | 93.9 |
| 16 | 14.5 | 12.8 | 94.1 |
| 17 | 23 | 12.4 | 94.6 |

The results in Table 4 show that calcination post-treatment periods as short as 1 hour give enhancements in activity and selectivity, while calcination periods of time between 4–14.5 hours give optimum improvements in catalytic activity (conversion of butadiene).

Examples 18–19

Effect of Cs-Promoter Loadings on Catalyst Deactivation and Reactivation

Two additional catalyst samples were prepared in a manner identical to that described above except for the Cs loadings. In both cases, the Cs component was added as CsCl salt. The first catalyst contained 766 ppmw Cs and 14.2 wt % Ag, and the second catalyst contained 826 ppmw Cs and 13.9 wt % Ag. Both catalysts employed SA-5562 α-alumina rings as the support. The effects of storage in amber bottles at ambient conditions on catalyst performance are summarized in Table 5 below. Example 18 shows the effect of catalyst aging (stored in amber glass bottles at ambient conditions) for the composition containing 766 ppmw Cs and 14.2 wt % Ag, while Example 19 shows the effect of catalyst aging at similar conditions for the sample containing 826 ppmw Cs and 13.9 wt % Ag.

TABLE 5

| | Example 18 | | Example 19 | |
|---|---|---|---|---|
| Age of Catalyst (days) | Butadiene Conversion (%) | Epoxybutene Selectivity (%) | Butadiene Conversion (%) | Epoxybutene Selectivity (%) |
| 1 | 15.0 | 94.0 | 14.6 | 94.2 |
| 6 | 14.9 | 93.5 | 14.3 | 93.8 |

TABLE 5-continued

|  | Example 18 | | Example 19 | |
| --- | --- | --- | --- | --- |
| Age of Catalyst (days) | Butadiene Conversion (%) | Epoxybutene Selectivity (%) | Butadiene Conversion (%) | Epoxybutene Selectivity (%) |
| 20 | 12.9 | 93.0 | 6.2 | 91.6 |
| 33 | 11.2 | 92.1 | 7.2 | 92.4 |
| 98 | 6.0 | 92.0 | 4.5 | 91.7 |

The data in Table 5 show that catalysts containing lower levels of Cs also undergo deactivation upon storage at ambient conditions. In case of Example 18, a catalyst containing 766 ppmw Cs, 60% of the initial catalyst activity was lost after storage under ambient conditions for 98 days. Similarly, Example 19 (826 ppmw Cs) indicates 69.1% of the initial activity was lost after storage under ambient conditions for 98 days.

By comparison, the catalyst of Example 1 (1046 ppmw Cs) lost 80% of its initial activity after 86 days of storage in amber bottles under ambient conditions. These results indicate that all Cs-promoted catalysts lose activity upon storage under ambient conditions of moisture and that the rate of activity loss is higher with increasing Cs loadings. Thus, Cs-promoter loadings less than 766 ppmw Cs would also undergo deactivation, although at lower rates than the examples presented here. Consequently, reactivation at elevated temperatures in flowing air would increase the catalytic activities of all Cs salt-promoted, Ag catalysts.

In a more general perspective, reactivation by calcination in flowing air (or other gas composition) should increase the catalytic activities of all Ag-containing catalysts for olefin epoxidation reactions that are promoted with moisture-sensitive alkali metal salts.

Examples 20–22

Effect of Gas Composition on Post-Treatment Calcination Process

Portions of the catalyst described in Example 1 were re-evaluated after 23–26 days of storage in an amber container stored under ambient laboratory conditions of temperature and moisture. The gas compositions of each of the post-treatments are shown in Table 6 below. In each case, the total gas flow was 100 ml/min (STP). The catalyst samples were given post-treatments "in situ" after being placed in the tubular reactor used for catalyst evaluation. The 3.0-gram samples were evaluated immediately after the post-treatment sequence.

TABLE 6

| Example No. | Days of Storage | Post-Treatment Gas Composition | Butadiene Conversion (%) | Epoxybutene Selectivity (%) |
| --- | --- | --- | --- | --- |
| From Ex. 1 | 21 | none | 3.2 | 90.7 |
| 20 | 23 | 20% $H_2$/80% He | 9.7 | 94.1 |
| 21 | 23 | 20% $O_2$/80% He | 8.9 | 96.1 |
| 22 | 26 | 100% He | 8.9 | 95.5 |

The results in Table 6 show that the composition of the gas stream used for the post-treatment process is not critical so long as the combination of post-treatment period of time and temperature is adequate to restore activity. The use of air may be preferred over inert gases and $H_2$-containing gas streams for cost and safety reasons. In all cases, however, the catalytic activities are greatly enhanced compared to the untreated sample.

While the invention has been described with reference to preferred embodiments and working examples, it is to be understood that variations and modifications may be resorted to as will be apparent to those skilled in the art. Such variations and modifications are to be considered within the purview and scope of the invention as defined by the claims appended hereto.

I claim:

1. A method for restoring lost activity and selectivity of fresh cesium-promoted catalysts, said method comprising the step of:
   heating said fresh cesium-promoted catalyst at a temperature between 150° C. and 350° C. in the presence of a sweep gas to restore said lost activity and selectivity immediately prior to using said catalyst.

2. The method according to claim 1, wherein said catalyst comprises silver.

3. The method according to claim 1, wherein said catalyst comprises a cesium promoter selected from the group consisting of cesium nitrate, cesium chloride, cesium bromide, cesium oxide, cesium hydroxide, cesium acetate, cesium sulfate, and cesium perrhenate.

4. The method according to claim 1, wherein said sweep gas is air, inert gas, or $H_2$-containing inert gas.

5. The method according to claim 1, wherein said sweep gas has a gas hourly space velocity of 10–10,000 $hr^{-1}$.

6. The method according to claim 1, wherein said sweep gas has a moisture content of 1000 ppm or less.

7. The method according to claim 1, which further comprises, following the heating step, the step of intimately contacting said catalyst with a gas stream comprising about 4 to 50% by volume of hydrogen at a temperature of about 170° C. to 400° C. and a gas hourly space velocity of about 10 to 10,000 $hr^{-1}$.

8. A method for restoring lost activity and selectivity of fresh cesium-promoted, silver catalysts, said method comprising the step of:
   heating said catalyst in flowing air at a temperature between 150° C. and 350° C. immediately prior to using said catalyst.

9. A method for preparing 3,4-epoxy-1-butene, which comprises:
   (a) heating a fresh cesium-promoted, silver catalyst at a temperature between 150° C. and 350° C. in the presence of a sweep gas to restore lost activity and selectivity of the catalyst; and immediately thereafter
   (b) contacting 1,3-butadiene with oxygen in the presence of said catalyst to form 3,4-epoxy-1-butene.

10. The method according to claim 9, wherein said sweep gas is air, inert gas, or $H_2$-containing inert gas.

11. The method according to claim 9, wherein said sweep gas has a gas hourly space velocity of 10–10,000 $hr^{-1}$.

12. The method according to claim 9, wherein said sweep gas has a moisture content of 1000 ppm or less.

13. The method according to claim 9, which further comprises, between steps (a) and (b), the step of intimately contacting said catalyst with a gas stream comprising about 4 to 50% by volume of hydrogen at a temperature of about 170° C. to 400° C. and a gas hourly space velocity of about 10 to 10,000 $hr^{-1}$.

14. The method according to claim 9, wherein said catalyst comprises a cesium promoter selected from the group consisting of cesium nitrate, cesium chloride, cesium bromide, cesium oxide, cesium hydroxide, cesium acetate, cesium sulfate, and cesium perrhenate.

* * * * *